United States Patent [19]

Jackson

[11] 3,971,855

[45] July 27, 1976

[54] PREVENTION OF FUNGI AND MOLDS IN POULTRY AND ANIMAL FEEDSTUFFS WITH METHYL ROSANILINE CHLORIDE ADDITIVE

[75] Inventor: Dennis E. Jackson, Springfield, Mo.

[73] Assignee: Naremco, Inc., Springfield, Mo.

[22] Filed: Dec. 11, 1974

[21] Appl. No.: 531,720

Related U.S. Application Data

[62] Division of Ser. No. 307,372, Nov. 17, 1972, abandoned.

[52] U.S. Cl. .............................. 426/321; 426/532; 426/540; 426/807
[51] Int. Cl.² .......................................... A23K 3/00
[58] Field of Search ............... 426/74, 97, 151, 177, 426/227, 310, 323, 335, 218, 807, 293, 295, 321, 532, 540, 648; 260/391; 252/400 R, 401

[56] References Cited
UNITED STATES PATENTS

| | | | |
|---|---|---|---|
| 2,124,590 | 7/1938 | Reed | 260/391 |
| 2,331,807 | 10/1943 | Shea | 426/97 |
| 2,946,722 | 7/1960 | Hoffman | 424/127 |
| 2,999,026 | 9/1961 | Davis | 260/391 |
| 3,146,162 | 8/1964 | Abramson | 260/391 |

FOREIGN PATENTS OR APPLICATIONS 463,449  5/1951  Italy

OTHER PUBLICATIONS

*The Cambridge Italian Dictionary*, vol. 1, 1962, p. 177.
*Webster's New World Dictionary*, 2nd College Edition, p. 1270, 1970.
*The Condensed Chemical Dictionary*, 8th Edition, pp. 781, 5, 102, 926.

Primary Examiner—Curtis P. Ribando
Attorney, Agent, or Firm—Bacon & Thomas

[57] ABSTRACT

An animal or poultry feed additive which is effective for inhibiting or preventing microbial activity, fungi and mold growth in feeds to which it is added provided by dispersing methylrosaniline chloride on an acid-treated mineral carrier.

5 Claims, No Drawings

PREVENTION OF FUNGI AND MOLDS IN POULTRY AND ANIMAL FEEDSTUFFS WITH METHYL ROSANILINE CHLORIDE ADDITIVE

This is a division of copending application Ser. No. 307,372, filed Nov. 17, 1972, now abandoned.

BACKGROUND OF THE INVENTION

1. Field of the Invention

This invention relates to animal and poultry husbandry and, in particular, to the provision of a feed supplement which can be readily mixed into animal and poultry feeds to effectively inhibit or prevent harmful microbial activity, fungi and mold growth in the feed. The invention also embraces methods for preparing the feed supplement and to feeds containing same.

2. Description of Prior Art

Due to steady changes in the ecology resulting from introduction of more intensive methods of farming, and increasing use of chemicals which alter the microbial populations of soils, plants, etc., the growth of toxin producing and infectious molds in both human foods and animal feedstuffs has during recent years become a matter of increasing concern for both animal and human welfare. Considerable research has been devoted to the development of methods for inhibiting mold growths in poultry and animal feeds. Heating of freshly ground feeds, a result of stimulation of mold growth as moisture is released during grinding and processing, is now a widely occurring problem. Mold growths are activated directly in proportion to the moisture content of the feedstuffs., i.e., the greater the moisture content, the greater the hazard of mold growths, and the production of growth inhibiting toxins.

Methylrosaniline chloride (Gentian Violet or Crystal Violet) is known to be an effective mold and fungi inhibitor. Hoffman and Scott, U.S. Pat. Nos. 2,946,722 and 3,231,466 discloses the incorporation of this substance into animal and poultry formulations with the objective of inhibiting the growth of molds and specific bacteria in the contents of the guts of animals and birds. In its solid form, however, methylrosaniline chloride cannot be uniformly dispersed in feedstuffs. It is electrostatic and therefore the particles tend to cling together. This problem has been solved by dissolving methylrosaniline chloride in a volatile organic solvent, dispersing the solution in a premix and incorporating the premix in the animal or poultry ration.

SUMMARY OF THE INVENTION

I have now discovered that the effectiveness of methylrosaniline chloride for inhibiting or preventing microbial activity, fungi and mold growths in feedstuffs is considerably enhanced by the treatment of a premix or carrier on which the methylrosaniline chloride is dispersed with a small amount of an acid. The acid may be adsorbed by the carrier or may react to form non-toxic water soluble salts with the constituents of the premix or carrier. In any event, the presence of the acid or its reaction products in intimate contact with the methylrosaniline chloride appears to more effectively release this mold-inhibiting material in the feed environment when it is needed.

It is an object of the invention to provide a methylrosaniline chloride product which can be readily dispersed in feedstuffs and from which the methylrosaniline chloride is effectively released in the presence of moisture in the feedstuff environment.

Another object of the invention is to provide an animal or poultry feedstuff which is effectively inhibited from the growth of infections molds and toxins.

A further object of the invention is to provide a method for dispersing methylrosaniline chloride in feed additives and feedstuffs.

DETAILED DESCRIPTION

The invention, in one aspect, relates to an additive for poultry or animal feeds which comprises a finely-divided, acid-treated, non-toxic carrier having methylrosaniline chloride uniformly dispersed thereon and to a feedstuff with which such additive is thoroughly mixed. In another aspect, the invention relates to a method of incorporating methylrosaniline chloride into carriers and feedstuffs for uniform dispersion and effective release.

Suitable carriers include any of a wide variety of substances which can be incorporated into feedstuffs without adverse effect, and preferably with beneficial effect, upon the animals or birds which consume the feedstuff. Such carriers comprise natural minerals such as clays, diatomaceous earths, calcium or magnesium carbonates, phosphates or silicates and mineral salts of both organic and inorganic nature, such as the salts of trace element compounds commonly added to feedstuffs, e.g., magnesium, copper, iron, manganese, cobalt and zinc sulfates, citrates or choline citrates and combinations thereof. While any non-toxic, finely-divided solids, preferably of a mineral nature can be used, it is obviously advantageous to use those which, individually or in various combination (as in mineral premixes) can be factored into poultry or animal feeds as desirable or commonly used parts of the primary feed formula. The carrier may be a mineral premix or a component of such a premix. Examples of mineral additives and premix formulations are set forth in the aforementioned U.S. Pat. Nos. 2,946,722 and 3,231,466 and other premix formulations are well known in the art. Advantageously, finely divided limestone, dolomite, deflourinated rock phosphate, tricalcium phosphate, dicalcium phosphate or calcium carbonate may be used. Calcium carbonate or ground limestone are preferred materials because in minimal quantities they are components of substantially all formulated feedstuffs and when used as dispersing agents can be calculated by the nutritionist, the result in effect being that virtually no dilution of the nutrient value of the feedstuff occurs as a result of the addition of the mold inhibitor.

The acid used for treating the carrier is one which in the amounts used will not be harmful, either as such or in the form of its reaction products, in the feed product. The function of the acid, either as such or in the form of its reaction products, is to provide a material which is in intimate association with the methylrosaniline chloride on the carrier and which will facilitate release of the methylrosaniline chloride in the feedstuff environment. Organic acids, such as acetic, citric, propionic, butyric and lactic can be used, as well as mineral acids provided they do not form water-insoluble reaction products with the components of the carrier. Ordinary vinegar may be used to supply the acid.

The more finely-divided the carrier material the more thoroughly it can be incorporated into the feedstuff. This, of course, is an important consideration in view of the fact that quantities of additive as small as one-half pound per ton of feed or less may be incorporated in the feed product. In general, the amount of the additive would be in the range of about 0.01 to 5.0% depending on the concentration of methylrosaniline chloride in the additive. The carrier is preferably sufficiently finely divided as to pass through a 100 mesh standard sieve and conveniently is in the minus 325 mesh size range.

The methylrosaniline chloride is dissolved in a volatile organic solvent, such as an alcohol or ketone, for dispersion on the carrier. The acid can be included in the same solvent or can be added to the carrier before or after addition of the methylrosaniline chloride.

The percentage of methylrosaniline chloride incorporated in the carrier can be varied from minute but effective mold inhibiting amounts when the carrier is incorporated in the feed up to the maximum amount the particular carrier will tolerate and still retain its capacity for distribution in the feedstuff. Conveniently, the amount will be that which will provide the minimum quantity necessary for effective mold control when the carrier is mixed with the feed in the amount commonly used. Effective mold control has been obtained by use of the invention when as little as 8 grams of methylrosaniline chloride is present in the feed. Thus, if the normal requirement of calcium carbonate for a particular feed is 10 pounds per ton, the amount of methylrosaniline chloride to be incorporated in the calcium carbonate for addition to this feed would be about 0.2% by weight based on the weight of the calcium carbonate. However, no exact critical range may be specified. Effective mold control for some feeds may be obtained with less than 8 grams of methylrosaniline chloride per ton and others may require more. In general, it is contemplated that the amount of methylrosaniline chloride incorporated in the carrier would be in the range of about 0.05 to 5% based on the weight of the carrier and that this material would then be incorporated in the feedstuff at the rate of about 0.1 to 25 pounds per ton.

Likewise, no exact critical range can be given for the acid component. The amount of acid is such that an improvement in mold-inhibiting effectiveness of the methylrosaniline chloride in the feedstuff is realized. Generally, from about 0.1 to 10% by weight of the acid, based on the weight of the carrier is added.

In a typical method of manufacture the methylrosaniline chloride and acid are both dissolved in the volatile solvent and the resulting solution is added to the dry carrier material in a suitable mixer. Alternatively, separate solutions of methylrosaniline chloride and acid may be added to the dry ingredients in either order. Mixing can be continued until the materials are thoroughly mixed and the volatile solvent is substantially evaporated. Where reaction occurs between the carrier and acid some heat is given off which aids in the evaporation of the solvent. However, even without heating, a solvent which is sufficiently volatile, such as methyl alcohol, will substantially evaporate during mixing. A representative example is given below:

EXAMPLE 1

95.2 Parts by weight of −325 mesh calcium carbonate and 1.7 parts by weight of diatomaceous silica were placed in a vented, two-speed, stainless steel blender which was provided with micronizing blades to provide a "plough-shear" blending action. The blender was turned on at low speed to mix the dry ingredients. In the meantime 1.6 parts by weight of Gentian Violet (methylrosaniline chloride) and 1.0 parts by weight of acetic acid were dissolved in 1.5 parts by weight of methyl alcohol and 0.5 parts by weight of water. After the dry ingredients had mixed for about 5 minutes, the blender was turned on high speed and the solution was added slowly through an injector. After all the liquid had been added the blender was operated at high speed for another 15 minutes to allow for thorough dispersion of the Gentian Violet throughout the product, for evaporation of methyl alcohol and water and for evolution of carbon dioxide. The blender was then turned to low speed and the product was discharged and packed into appropriate containers. This product contained about 1.6% by weight of Gentian Violet.

EXAMPLE 2

The product of Example 1 is substituted for one pound of the ground limestone in the following poultry feed ration:

| INGREDIENTS | lb./ton |
|---|---|
| Ground yellow corn | 1290 |
| Soybean oil meal (50% protein) | 640 |
| Steamed bone meal | 40 |
| Ground limestone | 20 |
| Iodized salt | 10 |
| Minor amounts of vitamins, etc. | |

Likewise, the product may be incorporated in other basal rations for poultry, swine, cattle and horses.

Similarly, Gentian Violet and acid is incorporated in other mineral and mineral salt carriers in the appropriate amounts for the specific needs.

It will be noted that there is very little feed dilution when this mold inhibitor is used. No toxic or growth inhibiting stress on the animal or fowl consuming the inhibited feed has been found. Gentian Violet is not absorbed from the intestine of the bird or animal; therefore, it leaves no chemical residue which can become an undesirable component of human food. The Gentian Violet appears to be in the form of a surface coating on the carrier particles in intimate association with the acid or acid reaction products which have been formed in situ during the mixing operation.

Tests of anti-microbial activity indicate that Gentian Violet on the acid-treated mineral carrier is about ten times as effective in feeds as the same percentage of Gentian Violet dispersed on a carrier of vegetable origin such as corn cob meal.

I claim:

1. A poultry or animal feed product protected against microbial activity, fungi and mold growths, comprising a basal feed ration containing ground feed materials in intimate admixture with a substantially dry, finely-divided, non-toxic, mineral carrier having from about 0.05% to 5.0% by weight of methylrosaniline chloride dispersed thereon, said mineral carrier having incorporated therein by adsorption or reaction from about 0.1% to 10% by weight of a non-toxic acid based on the weight of the carrier, said acid being one which is adsorbed by or forms water soluble reaction products with said carrier, to thereby facilitate the release of said methylrosaniline chloride from the carrier in the presence of moisture.

2. The feed product of claim 1 wherein the acid-treated carrier contains from about 0.1 to 5% by weight, based on the weight of the carrier, of methylrosaniline chloride, and said acid-treated mineral carrier is present in the feed product in an amount of from about 0.1 to 25 pounds per ton of feed.

3. The feed product of claim 1 wherein the mineral carrier is a poultry feed supplement which has been treated with acetic acid.

4. The feed product of claim 1 wherein the mineral carrier is calcium carbonate which has been treated with acetic acid.

5. The feed product of claim 1 wherein the mineral carrier is selected from the group consisting of ground limestone, dolomite, defluorinated rock phosphate, tricalcium phosphate, dicalcium phosphate and calcium carbonate.

* * * * *